United States Patent
Bland

(10) Patent No.: US 7,528,286 B2
(45) Date of Patent: May 5, 2009

(54) 4-CHLORO-4-ALKOXY-1,1,1-TRIFLUORO-2-BUTANONES, THEIR PREPARATION AND THEIR USE IN PREPARING 4-ALKOXY-1,1,1-TRIFLUORO-3-BUTEN-2-ONES

(75) Inventor: Douglas C. Bland, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 12/147,912

(22) Filed: Jun. 27, 2008

(65) Prior Publication Data

US 2009/0005603 A1 Jan. 1, 2009

Related U.S. Application Data

(60) Provisional application No. 60/937,903, filed on Jun. 29, 2007.

(51) Int. Cl.
*C07C 45/61* (2006.01)
*C07C 49/16* (2006.01)
(52) U.S. Cl. .................. 568/404; 568/403; 568/419
(58) Field of Classification Search .............. 568/403, 568/404, 419
See application file for complete search history.

(56) References Cited

U.S. PATENT DOCUMENTS 5,708,175 A 1/1998 Koyanagi et al.
7,057,079 B2 6/2006 Braun et al.
2005/0070716 A1 3/2005 Braun et al.
2005/0288511 A1 12/2005 Hamilton et al.
2006/0084813 A1 4/2006 Hausmann et al.

FOREIGN PATENT DOCUMENTS

DE 1223821 9/1966
WO WO 2004/108647 A2 12/2004
WO PCT/US2008/068378 11/2008

OTHER PUBLICATIONS

McMahon, Edward M. et al.; Preparation and Properties of Ethyl Vinyl Ketone and of Methyl Isopropenyl Ketone; J. Am. Chem Society; Sep. 1948; pp. 2971-2977.
Tietze, L.F. et al; Synethesis of Alkyl Propanoates by a Haloform Reaction of a Trichloro Ketone: Preparation of Ethyl 3,3-DiethyoxyPropanoate; Organic Synetheses; pp. 238-245. 1990.
Iqbal, Javed and Srivastava, Rajiv Ranjan; Cobalt(II)Chloride Catalysed Cleavage of Ethers with Acyl Halides: Scope and Mechanism; Tetrahedron; 1991; pp. 3155-3170; vol. 47 No. 18/19.
Moriguchi, Takeshi and Endo, Takeshi; Addition—Elimination Reaction in the Trifluoroacetylation of Electron-Rich Olefins; J. Org Chem.; 1995; pp. 3523-3528.

*Primary Examiner*—Sikarl A Witherspoon
(74) *Attorney, Agent, or Firm*—Craig Mixan

(57) ABSTRACT

4-Chloro-4-alkoxy-1,1,1-trifluoro-2-butanones, prepared by reacting alkyl vinyl ethers with trifluoroacetyl chloride, are useful for preparing 4-alkoxy-1,1,1-trifluoro-3-buten-2-ones.

4 Claims, No Drawings

4-CHLORO-4-ALKOXY-1,1,1-TRIFLUORO-2-BUTANONES, THEIR PREPARATION AND THEIR USE IN PREPARING 4-ALKOXY-1,1,1-TRIFLUORO-3-BUTEN-2-ONES

BACKGROUND OF THE INVENTION

This application claims the benefit of U.S. Provisional Application Ser. No. 60/937,903 filed on Jun. 29, 2007. The present invention concerns novel 4-chloro-4-alkoxy-1,1,1-trifluoro-2-butanones, a process for their preparation and a process for using them to prepare 4-alkoxy-1,1,1-trifluoro-3-buten-2-ones.

4-Alkoxy-1,1,1-trifluoro-3-buten-2-ones are useful intermediates for preparing pesticides; see, for example, U.S. Patent Publication 2005/0288511. Their preparation has previously been described, for example, in U.S. Pat. Nos. 5,708,175; 7,057,079 B2; WO 2004/108647 A2; and U.S. Patent Application Publication 2006/0084813 A1. Unfortunately, 4-alkoxy-1,1,1-trifluoro-3-buten-2-ones are relatively expensive and somewhat unstable, i.e., it is recommended that they be stored under refrigeration. It would be desirable to have a less expensive process to prepare 4-alkoxy-1,1,1-trifluoro-3-buten-2-ones. It would also be desirable to have a more stable precursor which could be more easily transported and stored or, alternatively, could be easily generated in situ.

SUMMARY OF THE INVENTION

The present invention concerns novel 4-chloro-4-alkoxy-1,1,1-trifluoro-2-butanones, a process for their preparation and a process for using them to prepare 4-alkoxy-1,1,1-trifluoro-3-buten-2-ones. More particularly, the present invention concerns 4-chloro-4-alkoxy-1,1,1-trifluoro-2-butanones of the formula:

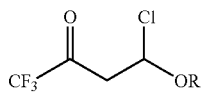

in which R represents a $C_1$-$C_8$ alkyl or phenyl.

Another aspect of the invention concerns a process for the preparation of 4-chloro-4-alkoxy-1,1,1-trifluoro-2-butanones of the formula:

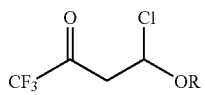

in which R represents a $C_1$-$C_8$ alkyl or phenyl which comprises contacting an alkyl vinyl ether of the formula

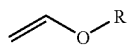

in which R is as previously defined with trifluoroacetyl chloride either neat or in the presence of an anhydrous organic solvent at a temperature from about −10° C. to about 35° C.

Another aspect of the invention concerns a process for the preparation of 4-alkoxy-1,1,1-trifluoro-3-buten-2-ones of the formula:

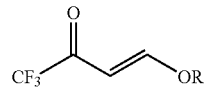

in which R represents a $C_1$-$C_8$ alkyl or phenyl which comprises contacting a 4-chloro-4-alkoxy-1,1,1-trifluoro-2-butanone of the formula:

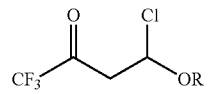

in which R represents a $C_1$-$C_8$ alkyl or phenyl, with a sulfoxide or a formamide catalyst of the formula

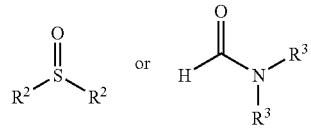

in which $R^2$ independently represents $C_1$-$C_8$ alkyl or phenyl, and
$R^3$ independently represents H, $C_1$-$C_8$ alkyl or phenyl, in the presence of an anhydrous organic solvent at a temperature from about −10° C. to about 20° C.

DETAILED DESCRIPTION OF THE INVENTION

The present invention concerns 4-chloro-4-alkoxy-1,1,1-trifluoro-2-butanones of the formula:

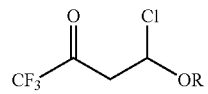

in which R represents a $C_1$-$C_8$ alkyl or phenyl. Unless specifically limited otherwise, the term "alkyl", as used herein, includes within its scope straight chain, branched chain and cyclic moieties.

The 4-chloro-4-alkoxy-1,1,1-trifluoro-2-butanones are prepared by reacting an alkyl vinyl ether of the formula

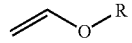

in which R represents a $C_1$-$C_8$ alkyl or phenyl, with trifluoroacetyl chloride.

Approximately equimolar quantities of alkyl vinyl ether and trifluoroacetyl chloride are generally used in the process, although excesses of one or the other may be employed. In practice, a 10-50 percent stoichiometric excess of alkyl vinyl ether is often preferred.

The reaction is conducted either in the absence of a solvent, e.g., with excess alkyl vinyl ether, or in the presence of an anhydrous organic solvent. Preferred solvents are hydrocarbon solvents, most preferably aromatic hydrocarbons such as toluene.

The reaction is conducted at a temperature from about −10° C. to about 35° C. Temperatures from about 0° C. to about 20° C. are usually preferred.

In a typical reaction, the trifluoroacetyl chloride is bubbled below the surface of the alkyl vinyl ether, either neat or in the presence of a hydrocarbon solvent, between 0-5° C. The reaction is allowed to warm with stirring for about one hour, keeping the temperature no higher than room temperature. The crude reaction mixture containing the 4-chloro-4-alkoxy-1,1,1-trifluoro-2-butanone is usually used as is without further isolation or purification of the reaction mixture.

The 4-chloro-4-alkoxy-1,1,1-trifluoro-2-butanones of the present invention are useful for preparing 4-alkoxy-1,1,1-trifluoro-3-buten-2-ones of the formula:

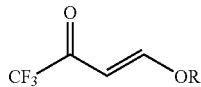

in which R represents a $C_1$-$C_8$ alkyl or phenyl by contacting the 4-chloro-4-alkoxy-1,1,1-trifluoro-2-butanone with a sulfoxide or a formamide catalyst of the formula

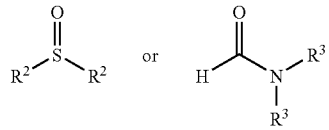

in which $R^2$ independently represents $C_1$-$C_8$ alkyl or phenyl, and $R^3$ independently represents H, $C_1$-$C_8$ alkyl or phenyl.

The sulfoxide or a formamide catalysts are generally employed at a level of from about 0.1 to about 10 mole percent based on the amount of 4-chloro-4-alkoxy-1,1,1-trifluoro-2-butanone. Levels of from about 0.5 to about 5 mole percent are usually preferred.

The reaction is conducted in the presence of an anhydrous organic solvent. Preferred solvents are hydrocarbon solvents, most preferably aromatic hydrocarbons such as toluene.

The reaction is conducted at a temperature from about −10° C. to about 20° C. Temperatures from about 0° C. to about 20° C. are usually preferred.

The 4-chloro-4-alkoxy-1,1,1-trifluoro-2-butanone is usually used as is without further isolation or purification of the reaction mixture. Thus, in a typical reaction, trifluoroacetyl chloride is bubbled below the surface of the alkyl vinyl ether in the presence of a hydrocarbon solvent, between 0-5° C. The reaction is allowed to warm with stirring for about 1 hour. The crude reaction mixture containing the 4-chloro-4-alkoxy-1,1,1-trifluoro-2-butanone is then cooled to between 0-5° C. and the sulfoxide or formamide catalyst is added in one portion. The reaction is generally complete after stirring for an additional 12-24 hours. The 4-alkoxy-1,1,1-trifluoro-3-buten-2-one is conveniently stored as is without further isolation or purification of the reaction mixture The following examples are presented to illustrate the invention.

EXAMPLES

Example 1

Preparation of
4-Chloro-4-ethoxy-1,1,1-trifluoro-2-butanone

To a 100 mL three neck round bottom flask fitted with a thermocouple and a dry ice/acetone condenser was charged with 26.4 g (0.37 mol) of ethyl vinyl ether. The reaction vessel was then submerged into an ice-water bath for cooling Then 49 g (0.37 mol) of trifluoroacetyl chloride was bubble subsurface through the reaction mixture. After completing the addition of the acid chloride, the ice-water bath was removed and the solution was allowed to warm to room temperature. The internal reaction temperature was not allowed to rise above 25° C. The reaction progress could be monitored by GC. GC analysis indicated that the reaction mixture contained un-reacted starting material. The reaction mixture was cooled in an ice-water bath and another 13 g (0.09 mol) trifluoroacetyl chloride was bubbled sub-surface through the reaction mixture. GC analysis indicated that the reaction still contained starting material so the process was repeated with another 19 g (0.14 mol) addition of trifluoroacetyl chloride. The reaction mixture was collected to give 58.6 g (~94% crude yield and ~71% pure by relative GC area) For 4-chloro-4-ethoxy-1,1,1-trifluoro-2-butanone: $^1$H NMR (CDCl$_3$, 300 MHz), δ 1.25 (t, J=6 Hz, 3H), 3.38 (dd, J=18.0, 3.0 Hz, 1H), 3.51 (dd, J=15.0, 9.0 Hz, 1H), 3.63 (dq, J=9.0, 6.0 Hz, 1H), 3.98 (dq, J=9.0, 6.0 Hz, 1H), 5.97 (dd, J=6.0, 3.0 Hz, 1H). GCMS (PCI-NH3): m/z 204.0165.

Example 2

Preparation of
4-Chloro-4-ethoxy-1,1,1-trifluoro-2-butanone

To a 50 mL three neck round bottom flask fitted with a thermocouple and a dry ice/acetone condenser was charged with 20 mL of toluene followed by 3.77 g (0.052 mol) of ethyl vinyl ether. The reaction mixture was then cooled in an ice-water bath and then 8.77 g (0.066 mol) of trifluoroacetyl chloride was bubbled sub-surface through the reaction mixture. The internal temperature rose from 3° C. to 5° C. The ice-water bath was removed and the solution was allowed to warm to ambient temperature and stir for an additional hour. Once the reaction was complete, GC analysis indicated the crude reaction mixture contained 4-chloro-4-ethoxy-1,1,1-trifluoro-2-butanone as the major product.

Example 3

Preparation of
4-Chloro-4-ethoxy-1,1,1-trifluoro-2-butanone

A 500 mL jacketed reactor was equipped with a cooling bath and mechanical stirring. To this vessel, blanketed with nitrogen, was charged 95.81 g (1.33 mol) of ethyl vinyl ether in one portion. The circulation bath temperature was set at 0° C., mechanical stirring was turned on, and the reactor contents were allowed to cool down. Once the internal reaction temperature reached about 2° C., then 148.1 g (1.12 mol) of trifluoroacetyl chloride was slowly bubbled through the reaction mixture via a subsurface dip tube over a 2.5 h period. The internal reaction temperature was kept below 12° C. by adjusting the rate of gas addition. Once the trifluoroacetyl chloride addition was completed, the subsurface dip tube was removed from the vessel and the reaction mixture was allowed to stir with cooling for an additional 1 h 27 min. The reaction mixture was bottom drained from the vessel to afford 232.1 g of a colorless liquid. $^{19}$F NMR assay of this mixture (using 98% 2,4-dichlorobenzotrifluoride as an internal standard) indicated a 93% isolated yield and 92% purity for 4-chloro-4-ethoxy-1,1,1-trifluorobutan-2-one.

Example 4

Preparation of 4-ethoxy-1,1,1-trifluoro-3-buten-2-one using dimethylsulfoxide as a catalyst The toluene solution of 4-chloro-4-ethoxy-1,1,1-trifluoro-2-butanone from Example 2 was then cooled to 2° C. using an ice-water bath and then 184 μL (0.003 mol) of dimethylsulfoxide-d$_6$ (DMSO) was added in one portion via syringe (note that there was some observed heat during this addition). The reaction was then stirred for 21 h at which time GC analysis indicated that the 4-ethoxy-1,1,1-trifluoro-3-buten-2-one was present in about 50% relative area percent. An additional 184 μL (0.003 mol) of DMSO-d$_6$ was added in one portion via syringe. A three degree heat rise was noticed during this second DMSO addition. The reaction was stirred an additional 3 h and then transferred to a glass bottle with a poly-seal cap. The product/toluene solution weighed 26.75 and was determined to contain 4-ethoxy-1,1,1-trifluoro-3-buten-2-one in about 65% "in pot yield" (based on starting ethyl vinyl ether molarity) by GC assay. GCMS: m/z found (M+1) 169.

Example 5

Preparation of 4-ethoxy-1,1,1-trifluoro-3-buten-2-one using dimethylformamide as a catalyst To a 50 mL three neck round bottom flask fitted with a thermocouple and a dry ice/acetone condenser was charged with 20 mL of toluene followed by 3.77 g (0.052 mol) of ethyl vinyl ether (EVE). The reaction mixture was then cooled in an ice-water bath and then 7.6 g (0.057 mol) of trifluoroacetyl chloride (TFAC) was bubbled sub-surface through the reaction mixture. The ice-water bath was removed and the solution was allowed to warm to ambient temperature (~20° C.) and stirred for an additional hour. GC analysis indicated that another addition of TFAC needed to be made. The reaction mixture was cooled using an ice-water bath and then another 2.1 g (0.016 mol) of trifluoroacetyl chloride was bubbled sub-surface through the reaction mixture. The cold bath was removed, and the solution was allowed to stir at ambient temperature for another 40 min. At this point, GC analysis indicated the crude reaction mixture contained 4-chloro-4-ethoxy-1,1,1-trifluoro-2-butanone as the major product. The reaction was then proceeded to the next step.

About 1 mL of the toluene solution of 4-chloro-4-ethoxy-1,1,1-trifluoro-2-butanone was set aside as a control reference. The rest of the toluene reaction mixture containing 4-chloro-4-ethoxy-1,1,1-trifluoro-2-butanone was then cooled to 2° C. using an ice-water bath. Then 400 μL (0.005 mol) of N,N-dimethylformamide-d$_7$ (DMF-d$_7$) was added in one portion via syringe. The reaction was then stirred for 24 h at which time GC analysis indicated that the 4-ethoxy-1,1,1-trifluoro-3-buten-2-one was present in about 57% relative area percent. The reaction mixture was then transferred to a glass bottle with a poly-seal cap. The product/toluene solution weighed 26.32 and was determined to contain 4-ethoxy-1,1,1-trifluoro-3-buten-2-one in about 62% "in pot yield" (based on starting EVE molarity) by GC assay.

What is claimed is:
1. A 4-chloro-4-alkoxy-1,1,1-trifluoro-2-butanone of the formula:

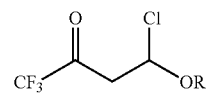

in which R represents a $C_1$-$C_8$ alkyl or phenyl.

2. A process for the preparation of 4-chloro-4-alkoxy-1,1,1-trifluoro-2-butanones of the formula:

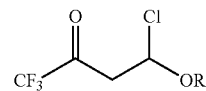

in which R represents a $C_1$-$C_8$ alkyl or phenyl
which comprises contacting an alkyl vinyl ether of the formula

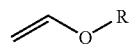

in which R is as previously defined with trifluoroacetyl chloride either neat or in the presence of an anhydrous organic solvent at a temperature from about −10° C. to about 35° C.

3. A process for the preparation of 4-alkoxy-1,1,1-trifluoro-3-buten-2-ones of the formula:

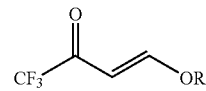

in which R represents a $C_1$-$C_8$ alkyl or phenyl which comprises contacting a 4-chloro-4-alkoxy-1,1,1-trifluoro-2-butanone of the formula:

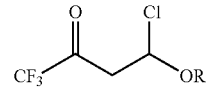

in which R represents a $C_1$-$C_8$ alkyl or phenyl, with a sulfoxide or a formamide catalyst of the formula

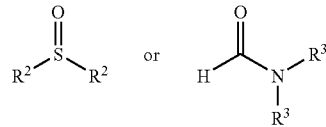

in which $R^2$ independently represents $C_1$-$C_8$ alkyl or phenyl, and $R^3$ independently represents H, $C_1$-$C_8$ alkyl or phenyl, in the presence of an anhydrous organic solvent at a temperature from about −10° C. to about 20° C.

4. A process for the preparation of 4-alkoxy-1,1,1-trifluoro-3-buten-2-ones of the formula:

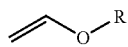

in which R represents a $C_1$-$C_8$ alkyl or phenyl which comprises:

a) contacting an alkyl vinyl ether of the formula

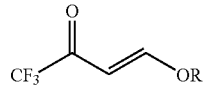

in which R is as previously defined with trifluoroacetyl chloride either neat or in the presence of an anhydrous organic solvent at a temperature from about −10° C. to about 35° C. to provide a 4-chloro-4-alkoxy-1,1,1-trifluoro-2-butanones of the formula:

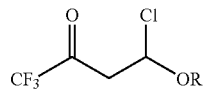

in which R represents a $C_1$-$C_8$ alkyl or phenyl; and b) contacting the 4-chloro-4-alkoxy-1,1,1-trifluoro-2-butanone of the formula:

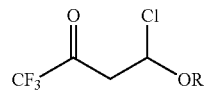

in which R represents a $C_1$-$C_8$ alkyl or phenyl, with a sulfoxide or a formamide catalyst of the formula

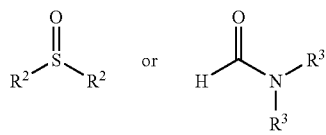

in which $R^2$ independently represents $C_1$-$C_8$ alkyl or phenyl, and $R^3$ independently represents H, $C_1$-$C_8$ alkyl or phenyl, in the presence of an anhydrous organic solvent at a temperature from about −10° C. to about 20° C.

* * * * *